US00PP26948P2

(12) United States Plant Patent
Kordes

(10) Patent No.: US PP26,948 P2
(45) Date of Patent: Jul. 19, 2016

(54) CLIMBING ROSE PLANT NAMED 'KORSWELUG'

(50) Latin Name: *Rosa hybrida*
Varietal Denomination: KORswelug

(71) Applicant: Tim-Hermann Kordes, Klein Offenseth-Sparrieshoop (DE)

(72) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 110 days.

(21) Appl. No.: 14/121,059

(22) Filed: Jul. 25, 2014

(51) Int. Cl.
*A01H 5/02* (2006.01)

(52) U.S. Cl.
USPC ..... Plt./114

(58) Field of Classification Search
USPC ..... Plt./114
See application file for complete search history.

(56) References Cited

PUBLICATIONS

HelpMeFind, http.www.helpmefind.com/rose/l.php?l=2.71328, downloaded Jan. 6, 2016.*

* cited by examiner

*Primary Examiner* — Anne Grunberg

(57) ABSTRACT

A new and distinct variety of rose with long lasting, novel pink flowers, and attractive foliage with very good disease resistance. It exhibits climbing growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORswelug'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present discovery constitutes a new and distinct variety of a garden rose plant which was discovered in a cultivated area in July 2010. The new rose variety resulted from a naturally occurring mutation of unknown causation on a branch of 'KORadigel', a climbing rose described in U.S. Plant Pat. No. 16,936, issued on Aug. 1, 2006.

The new rose plant was asexually propagated for evaluation. This new and distinctive climbing rose variety is named 'KORswelug'.

SUMMARY OF THE INVENTION

The new rose plant may be distinguished from its 'KORadigel', by the following combination of characteristics:

1. The general tonality of the blooms of 'KORswelug' is Red-Purple Group 62B, whereas the general tonality of 'KORadigel' is Red-Purple Group N66B.
2. After opening, the outer side of the outermost petals of 'KORswelug' are Red-Purple Group 73D, whereas the outer side of the outermost petals of 'KORadigel' after opening are Red-Purple Group 67B.

The new and distinctive rose plant was selected due to its:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORswelug' from all other varieties of which I am aware.

As part of a rose development program, Tim-Hermann Kordes asexually propagated the mutation by grafting and conducted evaluations and observations on the resulting plants in the inventor's nursery in Offenseth-Sparrieshoop, Germany. The first asexual propagation of 'KORswelug' was done by budding to seedling understocks in July 2012 at the inventor's nursery in Offenseth-Sparrieshoop, Germany.

This initial and other subsequent propagations conducted in controlled environments demonstrate that 'KORswelug' reproduces true to type in successive generations of asexual reproduction.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORswelug'.

DETAILED BOTANICAL DESCRIPTION

The following is a description of 'KORswelug', as observed growing in June 2014 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORuetroko', a rose variety from the same inventor described and illustrated in U.S. Plant Pat. No. 23,592 and issued on May 14, 2013 are compared to 'KORswelug' in Chart 1.

CHART 1

| Characteristic | 'KORswelug' | 'KORuetroko' |
|---|---|---|
| General tonality on open flower. | Red-Purple Group 62B. | Red Group 52B. |
| Average plant height. | 250 cm. | 150 cm. |
| Petal count under normal conditions. | Approximately 45 to 55 petals. | Approximately 160 to 190 petals. |

Parents:

*Parent*.—'KORadigel'.

Classification:

*Botanical classification*.—*Rosa hybrida* 'KORswelug'.

*Commercial classification*.—Climbing rose.

FLOWER AND FLOWER BUD

Blooming habit: Recurrent.

Flower bud:

*Size*.—Upon opening, 30 to 40 mm in length from base of receptacle to distal end of bud.

*Bud form*.—Pointed ovoid to ovoid.

*Bud color*.—As sepals first unfold, bud color is Red-Purple Group 62C. When ¼ open, the upper surface of petals is Red-Purple Group 62B, and the lower surface is Red-Purple Group 62C.

*Sepals*.—Color: Upper surface Green Group 138A. Lower surface Green Group 138A. Size: Average 12 mm (l)×6 mm (w). Shape: Weak foliaceous appendages on three of the five sepals. Apex: Cirrose. Base: Flat at union with receptacle. Quantity: Five. Surface texture: Upper side: Lightly pubescent. Lower surface: Lightly pubescent. Stipitate glands: Limited numbers present.

Flower bloom:

*Fragrance*.—Moderate to strong fragrance of citrus and spice.

*Duration*.—On the plant 3 to 5 days. Senesced petals drop away cleanly.

*Size*.—Large for a climbing rose. When open, the average flower diameter is 65 to 75 mm.

*Form*.—Shape of flower when viewed from the side: Upon opening, upper part: Flattened convex. Upon opening, lower part: Flattened convex. Open flower, upper part: Flat to flattened convex. Open flower, lower part: Flat to flattened convex.

Color:

*Upon opening, petals*.—Outermost petals: Outer Side: Red-Purple Group 73C. Inner Side: Red-Purple Group 65B. Innermost petals: Outer Side: Red-Purple Group 65B. Inner Side: Red-Purple Group 65B.

*Upon opening, basal petal spots*.—Basal petal spot, outermost petals: Outer Side: White Group 155C. Inner Side: White Group 155B. Basal petal spot, innermost petals: Outer Side: White Group 155A. Inner Side: White Group 155C.

*After opening, petals*.—Outermost petals: Outer Side: Red-Purple Group 73D. Inner Side: Red-Purple Group 65C. Innermost petals: Outer Side: Red-Purple Group 75C. Inner Side: Red-Purple Group 73D.

*After opening, basal petal spots*.—Basal petal spot, outermost petals: Outer Side: White Group 155C. Inner Side: White Group 155C. Basal petal spot, innermost petals: Outer Side: White Group 155B. Inner Side: White Group 155A.

General tonality: On open flower Red-Purple Group 62B. No change in the general tonality at the end of the 3rd day. Afterwards, general tonality is Red-Purple Group 62D.

Petals:

*Petal count*.—Very Double.

*Average range*.—Approximately 45 to 55 petals under normal conditions.

*Petal reflex*.—Petals reflex somewhat.

*Petal margin*.—Variable. Generally entire, however some notched and some with a point.

*Petal shape*.—Obovate. Apex: Obtuse. Base: Acute.

*Petal size*.—25 to 30 mm (l)×20 to 30 mm (w).

*Petal arrangement*.—Not formal.

*Texture*.—Smooth.

Petaloids:

*Petaloid count*.—Average of 8 to 12 per flower.

*Petaloid size*.—6 to 8 mm (l)×3 to 4 mm (w).

*Petaloid color*.—Inner side: Variable. Red-Purple Group 63B and Red-Purple Group 65B. Outer side: Variable. Red-Purple Group 63B and Red-Purple Group 65B.

*Petaloid texture*.—Smooth.

*Petaloid shape*.—Most commonly linear to elliptical.

Reproductive organs:

*Pistils*.—Approximately 40 to 45 present. Stigmas: Location: At the same position as the anthers. Color: Green-Yellow Group 1A. Styles: Length: About 10 mm long. Color: Green-Yellow Group 1A.

*Stamens*.—Approximately 40 to 45 on average and regularly arranged. Anthers: Size: Average 1.5 mm (l)×1 mm (w). Pollen: Limited. Color: Brown Group 200D. Filaments: Color: Green-White Group 157B. Length: 8 mm.

*Receptacle*.—Surface: Nearly smooth, with some fine hairs. Color: Green Group 138A with intonations of Greyed-Red Group 182B. Shape: Funnel-shaped. Texture: Smooth, lightly pubescent. Size: 6 mm (h)×8 mm (w).

*Pedicel*.—Surface: With small prickles. Length: 30 to 50 mm average length. Diameter: 2 to 3 mm average diameter. Color: Yellow-Green Group 146C. Intonations of Greyed-Red Group 182B and 182C. Strength: Strong. Texture: Smooth with small prickles. Borne: Multiple flower buds per stem, generally 5 to 7. Flowers slightly pendant.

*Peduncle*.—Surface: Nearly smooth, with some stipitate glands. Length: 40 to 60 mm average length. Diameter: 3 to 4 mm average diameter. Color: Yellow-Green Group 146B. Intonations of Greyed-Red Group 182C occasionally present. Strength: Strong. Borne: Multiple flower buds per stem, generally 5 to 7.

THE PLANT

*Growth*.—Vigorous growth.

*Plant habit*.—Upright climbing habit. When grown as a field plant, the average plant height is 250 cm and the average plant width is 100 cm.

*Stems*.—Stem color: Young wood: Green Group 138A. Older wood: Green Group 138A. Stem surface texture: Young wood: Smooth. Older wood: Smooth with some ridges.

*Prickles*.—Present. Incidence: Average of 5 per each 10 cm of stem. Size: Average length: 4 to 6 mm. Color: Immature prickles: Greyed-Red Group 179A. Mature prickles: Greyed-Red Group 179A. Senescing to Greyed-Orange Group 177D. Intonations: Greyed-Purple Group 183A. Shape: Deeply concave.

*Leaves*.—Normally 7 leaflets on normal leaves in middle of the stem. Venation pattern: Pyramidal net pattern. Leaf size: 100 mm (l)×60 to 70 mm (w). Abundance: Very abundant.

*Leaflets*.—Size: Average size of the terminal leaflet is 35 to 40 mm (l)×25 mm (w). Shape: Ovate. Base: Obtuse. Apex: Acute. Margins: Dentate. Surface: Glossy. Texture: Upper side of leaflet: Leathery. Under side of leaflet: Leathery. Color, mature foliage: Upper Leaf Surface: Green Group 139A. Lower Leaf Surface: Green Group 138A. Color, juvenile foliage: Upper Leaf Surface: Green Group 139A. Lower Leaf Surface: Green Group 138A. Anthocyanin intonation: Greyed-Purple Group 183B. Location: On immature foliage, upper and lower sides of leaflets. Arrangement: Odd pinnate. Venation: Reticulate.

*Stipules*.—Size: 10 to 12 mm (l)×5 to 6 mm (w). Stipule color: Green Group 139A. Stipitate glands: Present on margins. Margins: Bearded, serrated. Shape: Apex: Apiculate. Base: Winged.

*Petiole*.—Length: Average 10 to 15 mm. Diameter: Average 1.5 mm. Petiole color: Green Group 138A. Margins: With limited numbers of stipitate glands. Stipitate Glands: Limited numbers present on margins. Texture: Smooth.

*Petiole rachis*.—Color: Green Group 138A. Prickles: A few small prickles underneath. Stipitate glands: Limited numbers of stipitate glands on margins.

Hips/seed formation: None observed.

Winter hardiness: To date, the variety has been grown successfully in Zone 5.

Disease resistance: Very good resistance to powdery mildew (*Sphaerotheca pannosa*), blackspot (*Diplocarpon rosae*), and rust (*Phragmidium* sp) diseases under normal growing conditions in Jackson County, Oreg.

I claim:

1. A new and distinct variety of rose plant, as described and illustrated herein.

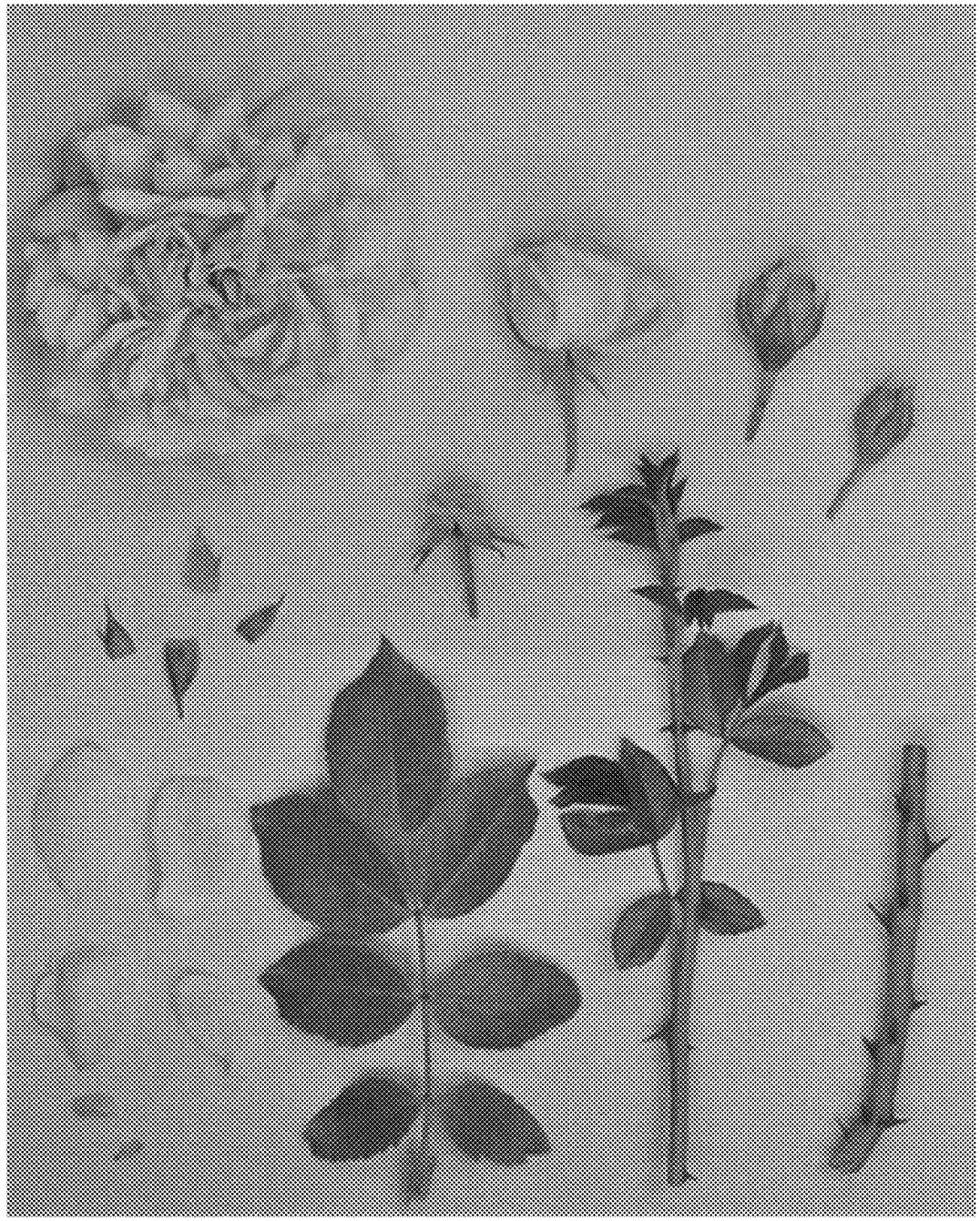

* * * * *